United States Patent [19]

Kosoburd et al.

[11] Patent Number: 5,760,871

[45] Date of Patent: Jun. 2, 1998

[54] DIFFRACTIVE MULTI-FOCAL LENS

[75] Inventors: Tatiana Kosoburd, Jerusalem; Joseph Kedmi, Rehovot; Israel Grossinger, Rehovot; Uri Levy, Rehovot, all of Israel

[73] Assignee: Holo-Or Ltd., Rehovot, Israel

[21] Appl. No.: 159,728

[22] Filed: Nov. 30, 1993

[30] Foreign Application Priority Data

Jan. 6, 1993 [IL] Israel .......................... 104316
Apr. 16, 1993 [IL] Israel .......................... 105434

[51] Int. Cl.⁶ .......................... G02C 7/04; G02B 5/18; G02B 3/14; A61F 2/16
[52] U.S. Cl. .......................... 351/161; 359/569; 359/571; 359/575; 359/665; 623/6
[58] Field of Search .......................... 351/160 R, 160 H, 351/161, 162; 359/569, 571, 574, 665; 623/6

[56] References Cited

U.S. PATENT DOCUMENTS

| | | | |
|---|---|---|---|
| 3,004,470 | 11/1961 | Ruhle et al. | 88/57 |
| 3,598,479 | 8/1971 | Wright | 351/159 |
| 4,162,122 | 7/1979 | Cohen | 351/161 |
| 4,174,156 | 11/1979 | Glorieux | 351/168 |
| 4,210,391 | 7/1980 | Cohen | 351/161 |
| 4,338,005 | 7/1982 | Cohen | 351/161 |
| 4,340,283 | 7/1982 | Cohen | 351/161 |
| 4,477,158 | 10/1984 | Pollock et al. | 351/169 |
| 4,704,016 | 11/1987 | de Carle | 351/161 |
| 4,828,558 | 5/1989 | Kelman | 351/172 |
| 4,830,481 | 5/1989 | Futhey et al. | 351/161 |
| 4,881,804 | 11/1989 | Cohen | 351/161 |
| 4,881,805 | 11/1989 | Cohen | 351/161 |
| 4,895,790 | 1/1990 | Swanson et al. | 430/321 |
| 4,936,666 | 6/1990 | Futhey | 350/452 |
| 5,073,007 | 12/1991 | Kedmi et al. | 359/565 |
| 5,076,684 | 12/1991 | Simpson et al. | 351/168 |
| 5,104,212 | 4/1992 | TaGoury | 351/160 |
| 5,114,220 | 5/1992 | Baude | 351/160 |
| 5,117,306 | 5/1992 | Cohen | 359/565 |
| 5,120,120 | 6/1992 | Cohen | 351/161 |
| 5,121,980 | 6/1992 | Cohen | 351/161 |
| 5,229,797 | 7/1993 | Futhey et al. | 351/161 |
| 5,344,447 | 9/1994 | Swanson | 351/161 |

FOREIGN PATENT DOCUMENTS

| | | |
|---|---|---|
| 0351471 | 1/1990 | European Pat. Off. . |
| 0367878 | 5/1990 | European Pat. Off. . |
| 0435525 | 7/1991 | European Pat. Off. . |
| 1154360 | 6/1969 | United Kingdom . |

OTHER PUBLICATIONS

H. Dammann, "Blazed Synthetic Phase–Only Holograms", Optik 31, Heft1 1970, pp. 95–104.

Dale A. Buralli et al, "Optical Performance of Holographic Kinoforms", Applied Optics, vol. 28(5), Mar. 1989, pp. 976–983.

Ora E.. Myers, Jr., "The Studies of Transmission Zone Plates", Uni. of Colorado, Boulder, Colorado, 1951.

Milton Sussman, "Elementary Diffraction Theory of Zone Plates" American Optical Company, Instrument Division, Buffalo, New York, 1959.

V.P. Koronkevitch, V.N. Nagorni et al., "Bifocus Microscope", Optik 78, No. 2, 1988, pp. 64–66.

Dammann, H. "Blazed Synthetic..." Philips Zentrallaboratorium GmbH, Laboratorium, Hamburg. pp. 95–104.

*Primary Examiner*—Scott J. Sugarman
*Attorney, Agent, or Firm*—Ladas & Parry

[57] ABSTRACT

A tri-focal diffractive lens defining three foci, for viewing a band of light having a representative wavelength of $\lambda$, including a diffractive surface having a number of optical heights, $h_o$, wherein the difference between the highest and the lowest optical heights is, modulo $\lambda$, substantially different from $\lambda/2$, wherein each of the foci receives at least 20% of light incident on the lens.

40 Claims, 8 Drawing Sheets

DIFFRACTIVE MULTI-FOCAL LENS

FIELD OF THE INVENTION

The present invention relates to multiple focus lenses in general and, more particularly, to multi-focal, diffractive, ophthalmic lenses.

BACKGROUND OF THE INVENTION

There are many applications for lenses which have more than one focal length. While there are important applications for multiple focus lenses in microscopes and other optical systems, the main effort spent in the development of multi-focal lenses is directed towards human vision correction, and especially towards construction of efficient multi-focal intraocular and contact lenses (collectively referred to herein as "ophthalmic lenses"). Since the fraction of incident light which is utilized by a multiple focal lens is divided between the different focal lengths, such lenses should be constructed to yield high light transmission efficiency. The need for such improved efficiency is particularly important for intraocular multi-focal lenses, since human vision is poor at low light levels.

Generally speaking, there are two basic approaches to the design and construction of a multiple focal lens, namely, the spatial division approach and the multiple diffraction approach.

Figure 1:
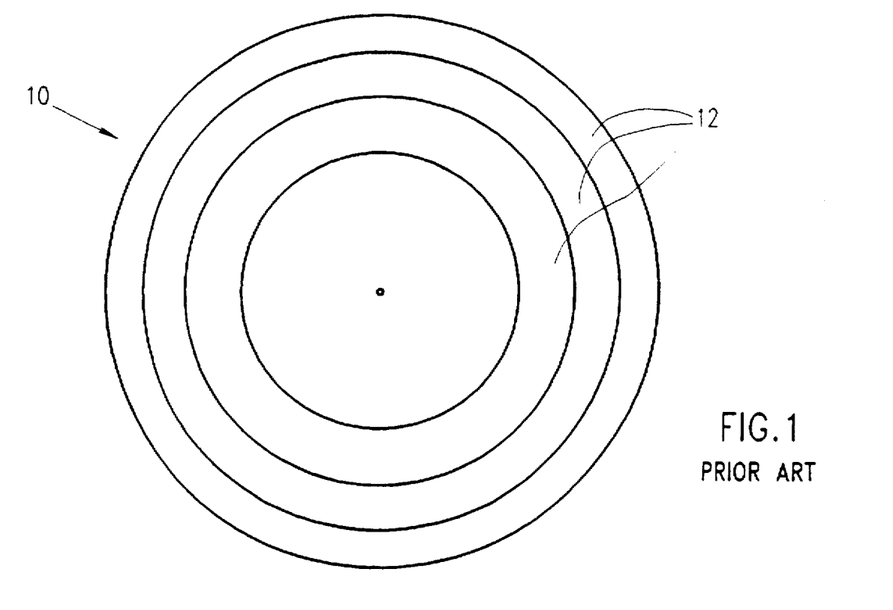
FIG. 1 is a transverse illustration of a prior art multi-focal refractive lens.

FIG. 1, which is an anterior view illustration of a multifocal lens 10, shows a spatially divided lens. The lens is sectioned into discrete, adjacent, refractive sections 12 which are, normally, concentric. The non-adjacent sections are grouped into a number of groups (typically two), wherein each group corresponds to a single-focus refractive lens, and wherein each section is an optical equivalent of a portion of the corresponding lens. Thus, each group is a spatially discontinuous, single-focus, refractive lens.

Since all incident light passing through each refractive group is focused in accordance with only one, respective, focal length, the fraction of total incident energy focused in accordance with each focal length is, optimally, equal to the fractional area of incidence covered by the respective refractive group.

To achieve good results in ophthalmic lenses, it is usually necessary that lens 10 comprise a large number of sections 12. If the lens is divided into a small number of concentric sections, the relative intensities of the different groups might vary in accordance with the expansion and contraction of the eye pupil.

U.S. Pat. Nos. 4,162,122 and 4,210,391 are concerned with refractive contact lenses which are divided into many concentric annular sections, wherein any two adjacent sections belong to two different focal groups. An attempt to spatially divide a contact lens into non-concentric sections is described in U.S. Pat. No. 4,704,016.

Figure 2:
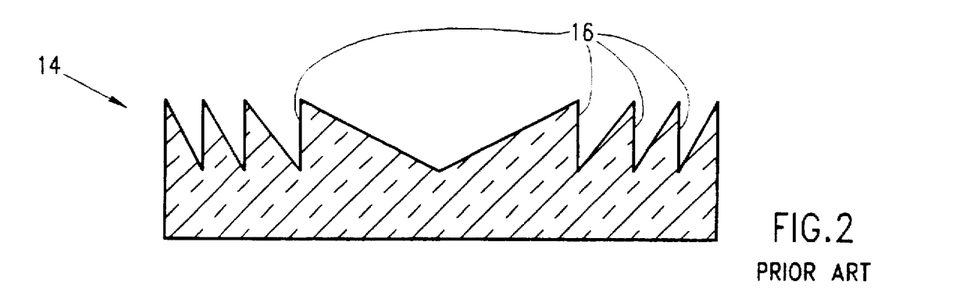
FIG. 2 is a radial, cross-sectional, illustration of a prior art bifocal diffractive lens.

As can be seen in FIG. 2, a diffraction lens 14 is generally constructed in accordance with a diffractive pattern, i.e. a locally periodic structure which affects the phase and/or amplitude of incident light. This results in a corresponding, transverse, locally periodic, relative-phase structure of the exiting wave front, thereby producing a multi-order diffraction image. By properly constructing a variable-period diffractive pattern, a given diffraction order may be focused onto a respective image plane on which it constructively interferes.

It should be appreciated that the different foci of diffractive lenses do not correspond to different zones of diffraction lens 14. Rather, every point of lens 14 diffracts the incident light into the different diffraction orders which correspond to the different foci.

A well known approach to the construction of diffractive patterns involves the use of Fresnel zone plates or Fresnel phase plates, which produce a variety of spherical wave fronts having different radii of curvature, wherein each radius corresponds to a different diffraction order. This general approach is described in "The Studies of Transmission Zone Plates", by Ora E. Myers, Jr., University of Colorado, Boulder, Colo., 1951 and in "Elementary Diffraction Theory of Zone Plates", by Milton Sussman, American Optical Company, Instrument Division, Buffalo, N.Y., 1959.

Prior art Fresnel phase plates have a typical general structure, which can be seen in FIG. 2, wherein the diffractive pattern comprises a series of one-way optical steps 16. Optical steps 16 are defined by sharp drops "d" in lens thickness, which cause a proportional phase difference between adjacent light rays passing through opposite sides of step 16. Typically, for bifocal diffractive lenses, the phase delay caused by drop "d" in height of steps 16 is equal to one half of a design wavelength "λ" which is typical of the wavelengths viewed with the lens. It has been generally believed that best results are achieved when there are a large number of steps and when the drops are very sharp, because some of the incident energy would not, otherwise, be focused to either of the foci.

U.S. Pat. Nos. 4,830,481 and 5,076,684 both describe such lenses. U.S. Pat. No. 4,830,481 appears to suggest that the sharp drop "d" can be smoothed to a limited extent, by curving the sharp corners in accordance with a limited radius of curvature (specifically, not more than one or two times the step height), sacrificing just a small fraction of the incident energy. Nevertheless, this reference teaches that some sacrifice in efficiency is a result of such a "smoother" lens.

Figure 3:
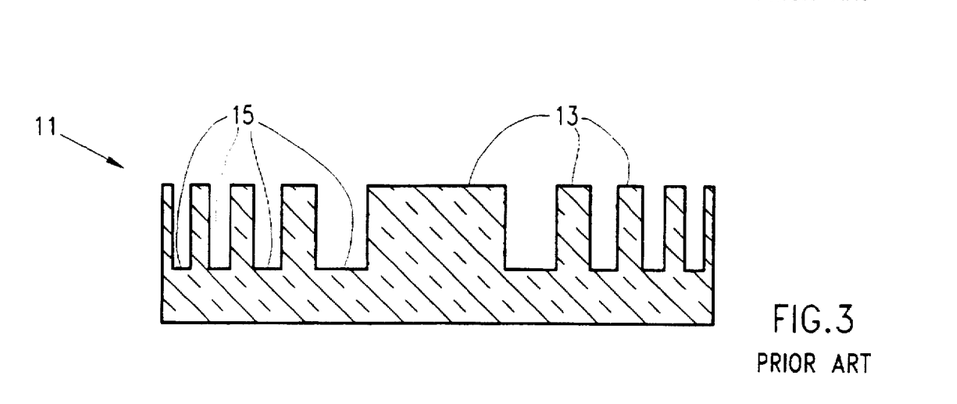
FIG. 3 is a radial, cross-sectional, illustration of a prior art Raleigh-Wood lens.

A bifocal diffraction Raleigh Wood lens is used in the bifocal microscope described in "Bifocus Microscope" by V. P. Koronkevitch, V. N. Nagorni, I. G. Palchikova and A. G. Poleshchuk, Optik 78, No. 2, 1988, pp. 64–66. As can be seen in FIG. 3, such a Raleigh Wood lens 11 consists of a series of rectangular protrusions 13 separated by a series of rectangular recesses 15, wherein the width of each protrusions is substantially equal to the width of an adjacent recess, i.e. a duty-cycle of 0.5, and wherein the phase difference between the protrusions and the recesses, i.e. the step height, is approximately equal to $\lambda/2(n_2-n_1)$, where $\lambda$ is the typical wavelength used and $n_1$, $n_2$ are the refractive indices of the lens and the material outside the lens. The lens is described as having a light transmission efficiency of 81% divided equally between intense "−1" and "+1" diffraction orders, whereas other orders are negligible. This lens has a topographical structure which is periodic in $r^2$.

There have also been attempts to construct a contact lens which combines advantageous features of both the spatial division and the diffraction order approaches. A lens can be spatially divided into narrow refractive concentric sections which are also diffractive phase-shift plates, spaced by precalculated distances, such that some diffraction order foci coincide with the refractive foci. Examples of such combinations is described in U.S. Pat. Nos. 4,338,005, 4,340,283, and 4,881,805, all issued to Cohen.

Considerable efforts have been directed toward controlling the relative intensities of the different orders in bi-focal lenses, by proper engineering of the diffractive structure, so that most of the incident energy is utilized by the orders which create the desired foci. Still, existing diffraction lenses having more than two foci and/or featuring a distinctively uneven distribution of light between the foci do not yield high light transmission efficiencies.

Moreover, the surfaces of the more efficient of the currently available bi-focal ophthalmic lenses (refractive, diffractive or hybrid) include a series of sharp edged steps, which define a plurality of sharp corners. The sharp edges and corners present inevitable difficulties for the user of the lens. First, dirt which is easily collected at the sharp corners is extremely difficult to remove by conventional cleaning instruments and materials. Secondly, the edges of the optical steps can cause undesirable light interference, known as glare, which appear to the eye of the user as disturbing blurry intense light. Thirdly, the sharp edged surface can cause uncomfortable irritation to the eyes of the user when the lens is used as a contact lens.

At present, only bi-focal ophthalmic lenses featuring a substantially even distribution of light between their two foci are available. This limitation is especially critical for intraocular lenses where the eye itself has no focusing power. With two focal lengths, the user is often deprived of clear vision in the mid range. There is therefore a need for an efficient intraocular lens having more than two focal lengths. Also, uneven intensity distribution between the foci may be desired such that vision of a preselected distance ranges will be particularly enhanced. For example, reading may require higher transmission efficiency than the efficiency required for viewing landscapes due to the generally different available light intensities.

U.S. Pat. Nos. 5,117,306; 5,121,980 and 5,120,120 to Cohen, describe various forms of bi-focal lenses.

SUMMARY OF THE INVENTION

The present invention provides improved solutions to the above mentioned problems associated with ophthalmic multi-focal diffractive lenses. A lens constructed and operative in accordance with a preferred embodiment of the present invention effectively focuses incident light in accordance with two or more different focal lengths simultaneously, and maintains an over all light transmission efficiency for more than two foci which is generally comparable with and often substantially better than bi-focal diffraction lenses. The high total light transmission efficiency is substantially maintained, in a preferred embodiment of the invention, regardless of whether the incident light is distributed evenly or unevenly among the different foci.

The present invention also provides an extremely efficient ophthalmic multi-focal diffractive lens having a preselected number of dominant foci and having a preselected distribution of incident light among the different foci. The preselected distribution may be even or uneven.

Surprisingly, the other problems of many existing ophthalmic lenses, namely those associated with a sharp stepped surface, are also solved by the present invention. The surfaces of a lens constructed and operative in accordance with a preferred embodiment of the invention are extremely smooth compared to those of most known diffraction and refraction multi-focal ophthalmic lenses.

In accordance with one preferred embodiment of the present invention there is thus provided a lens including a diffractive surface. The diffractive surface is constructed so that its radial cross-section is shaped in accordance with a diffractive pattern which diffracts most of the incident light energy into three dominant diffraction orders, namely, "−1", "0" and "+1". The "+1", "0" and "−1" diffraction orders conventionally represent convergingly diffracted light, divergingly diffracted light and undiffracted light, respectively. In a preferred embodiment, the incident energy is distributed substantially evenly among the three orders so that each of the three orders carries approximately one third of the transmitted energy.

In another preferred embodiment of the invention, the amount of light in the orders is not equal so as to account for the normal lighting conditions of objects at different distance ranges.

In lenses having even or uneven division of light, a substantial proportion of the total light is directed into each of the orders and, hence, the contrast at each of the foci is high. In accordance with a preferred embodiment, the dominant diffraction orders are preselected and the distribution of light among the dominant orders is preset.

A lens constructed in accordance with a preferred embodiment of the present invention is further provided with refractive power. The surfaces of the lens are appropriately constructed so that undiffracted incident light coming to the lens from a preset distance, which is preferably within an intermediate distance range (i.e. more than reading distance and less than infinity), is refractively focused (with the possible aid of the natural lens and/or cornea of the human eye) onto a given image plane (typically, a human eye retina).

In accordance with a preferred embodiment of the invention, light from the preset distance defined by the refractive surface is carried onto the image plane by the "0" order, which represents light which is unaffected by the diffractive surface. The "−1" order, representing light which is diverged by the diffractive surface, focuses light from a longer range (typically infinity) onto the same image plane. The "+1" order, representing light which is converged by the diffractive surface, focuses light from a shorter range (typically reading distance) onto the same image plane.

In accordance with a preferred embodiment of the invention, the topographical height at any given point on the diffractive surface (i.e. the separation of a given point on the diffractive surface with respect to a base reference surface corresponding to the general curvature of the diffractive surface) is generally a smooth, essentially periodic, function, h, of a function, u(r), of the radial coordinate, r. Furthermore, each period of this periodic function of u(r) is essentially symmetric with respect to u(r). Thus, the periodic function defines gradual, generally symmetric, rising and falling slopes between generally smooth peaks.

This periodic topographical height function "h", defines an optical height function "$h_o$" which is equal to "h" multiplied by ($n_2-n_1$), where $n_2$ and $n_1$, are the refractive indices of the lens material and the surrounding medium (typically air, eye tears of the intraocular fluid), respectively.

In accordance with particularly preferred embodiments of the invention the optical height function is different from $\lambda/2$, modulo $\lambda$.

In an alternative preferred embodiment of the invention the optical height function is a periodic function, $h_o$, of a function, u(r), of the radial coordinate but the function, $h_o$, is not symmetric. That is to say, during one portion of the period the function of the radial coordinate is different from that in a second portion of the period. More preferably, the spatial frequency of one portion is greater than that of the second portion.

In one embodiment of the present invention, the surface topographical function, h, defines essentially rectangular protrusions which are separated by essentially rectangular recesses. The step height of the protrusions determines the absolute intensity of each order as well as the relative intensities among the three diffraction orders. By properly selecting the height and optionally adjusting the "duty cycle" of the recesses (the proportion of the spatial cycle at during which there is protrusion), it is possible to equally divide the diffracted energy among the three orders, maintaining a reasonable imaging efficiency of close to 29% (i.e. image to background light intensity ratio) in each order, for a total of 86%. Furthermore, a high efficiency can be maintained for uneven distributions as well. Generally speaking, the optical height of the step is substantially less than $\lambda/2$.

In another embodiment of the invention, the diffractive surface follows a trapezoidal wave topographical pattern. The computed imaging efficiency obtained by this embodiment is 92.1%.

In one particularly preferred embodiment of the invention, the topographical optical height, $h_o$, of any given point on the diffractive surface of the lens, follows the formula: $A \cdot \cos(k \cdot r^2 + \phi) + C$, wherein "r" is the radial coordinate and A, k, and C are preselected parameters which are selected so as to yield the highest possible imaging efficiency. $\phi$ is a constant. This embodiment is preferred over the trapezoidal embodiment, because it combines the smoothness of a sinusoidal pattern with efficiency comparable to that of the trapezoidal pattern. This very smooth embodiment yields an imaging efficiency of approximately 90%.

Numerical analysis of the formula which is presented in the previous paragraph shows that optimal efficiency is achieved when the following parameters are used: $k=\pi/(\lambda f)$ and $A \approx 0.228\lambda/(n_2-n_1)$, wherein: "$\lambda$" is the wavelength at the center of the typical bandwidth which is viewed with the lens (typically in the visible spectrum), "f" is the desired first order focal length and $n_2$ and $n_1$ are the refractive indices of the lens and its surrounding medium, respectively.

For desired uneven distributions among the three orders, additional smaller steps are preferably added to the rectangular profiles, the slopes of the trapezoids are made unequal for the "rising" and "falling" portions and, for the sinusoidal function, the sinusoidal frequency is made different for two portions of the period.

In a accordance with another particularly preferred embodiment of the invention, the topographical optical height of the surface follows a generally periodic function of the radial coordinate, wherein each period of the periodic function follows the polynomial function:

$$h_o = \sum_{i=1}^{n} a_i u^i,$$

wherein ($0 \leq u \leq 2\pi$) is the normalized periodic variable (i.e. u is reset to zero at the beginning of each period of the periodic function) and wherein the $a_i$, are calculated using numerical optimization methods. Preferably, the radial width of a given period of the periodic function is inversely proportional to $r^2$, wherein "r" is the radial distance between the center of the given period and the center of the lens. By proper application of the numerical optimization methods, the transmission efficiency of each of the dominant diffraction orders is brought to a preselected target value. The resultant topographical function may be locally symmetric, typically when the target values represent an even efficiency distribution among the participating orders, or locally asymmetric, when the target values are uneven.

In accordance with yet another particularly preferred embodiment of the invention, each period of the topographical optical height function follows a "super Gaussian" function of the form: $H \cdot \exp\{-[(u-\pi)/W]^n\}$, wherein the parameters H, W and n are optimized using numerical optimization methods and wherein u is, again, a normalized periodic variable.

Alternatively, for an asymmetric distribution of transmission efficiencies, an asymmetric super Gaussian of the form:

$$H \cdot \exp\{[(u-u_0)/W_1]^{n_1}\} \text{ for } u \leq u_0;$$

and $$H \cdot \exp\{[(u-u_0)/W_2]^{n_2}\} \text{ for } u \geq u_0$$

is used. In this preferred embodiment of the invention H, $W_1$, $W_2$, $n_1$ and $n_2$ are optimized using numerical optimization methods. $u_0$ is equal to $2\pi W_1/(W_1+W_2)$. This shape provides superior bi-focal and tri-focal lenses.

In a preferred embodiment of the present invention, the lens includes an aspheric surface. The aspheric surface is operative to compensate for optical aberrations which are typical of spherical optics. In a preferred embodiment, the posterior surface of the lens is the aspheric surface and, more preferably, the posterior surface is constructed to precisely fit the aspheric surface of the human cornea. In a preferred embodiment, the aspheric optical properties of the aspheric surface are provided by refractive power, diffractive power or both.

A multi-focal contact lens constructed in accordance with a preferred embodiment of the present invention has such a smooth diffractive surface that, even when being in contact with the cornea, does not generally irritate the eye of the user. Therefore, it is possible that the posterior surface, i.e. the surface facing the human eye cornea, of such a contact lens may possess diffractive properties. Alternatively, it is possible that the anterior surface of the lens is diffractive.

In another preferred embodiment of the invention, the diffractive surface may be an interior surface of a sandwich lens structure. Preferably, such a sandwich lens is formed of two portions having respectively facing surfaces, at least one of which being diffractive. More preferably, the two portions of the sandwich lens have different refractive indices and neither of the external (i.e. not interfacing) surfaces of the two portions are diffractive. In a particularly preferred variant of this embodiment, especially useful for contact lenses, the outer portion is formed of a relatively hard material and the inner portion (next to the cornea) is formed of a relatively soft material.

In addition to their ophthalmic applications, multi-focal diffraction lenses constructed in accordance with preferred embodiments of the present invention can be used in various other multi-focal optical systems. Such multi-focal systems include, for example, multi-focal microscopes.

In a general aspect, the invention provides a tri-focal lens having a distribution among at least three dominant diffraction orders, wherein the efficiency of each dominant order is not lower than 20% and the sum of the efficiencies of all the dominant orders is at least 60% and more preferably over 80%.

In another general aspect, the invention provides a multi-focal diffractive lens including a diffractive surface, having a surface topography which includes local minima and maxima, operative to focus light in accordance with a plurality of dominant diffraction orders defining a plurality of respective foci, wherein the imaging efficiency of each of the orders is not less than twenty percent and wherein the radius of curvature of the diffractive surface, at any given point on the surface, is equal to at least twice the difference in topographical height between the local minimum nearest to the given point and the local maximum nearest to the given point. In a preferred embodiment of the invention, the radius of curvature at any point on the surface is equal to at least 10 or, more preferably, 100 times the difference in topographical height between the nearest local minimum and the nearest local maximum.

BRIEF DESCRIPTION OF THE DRAWINGS

The present invention will be better understood from the following description of the preferred embodiments together with the following drawings of which.

DETAILED DESCRIPTION OF PREFERRED EMBODIMENTS

Figure 4A:
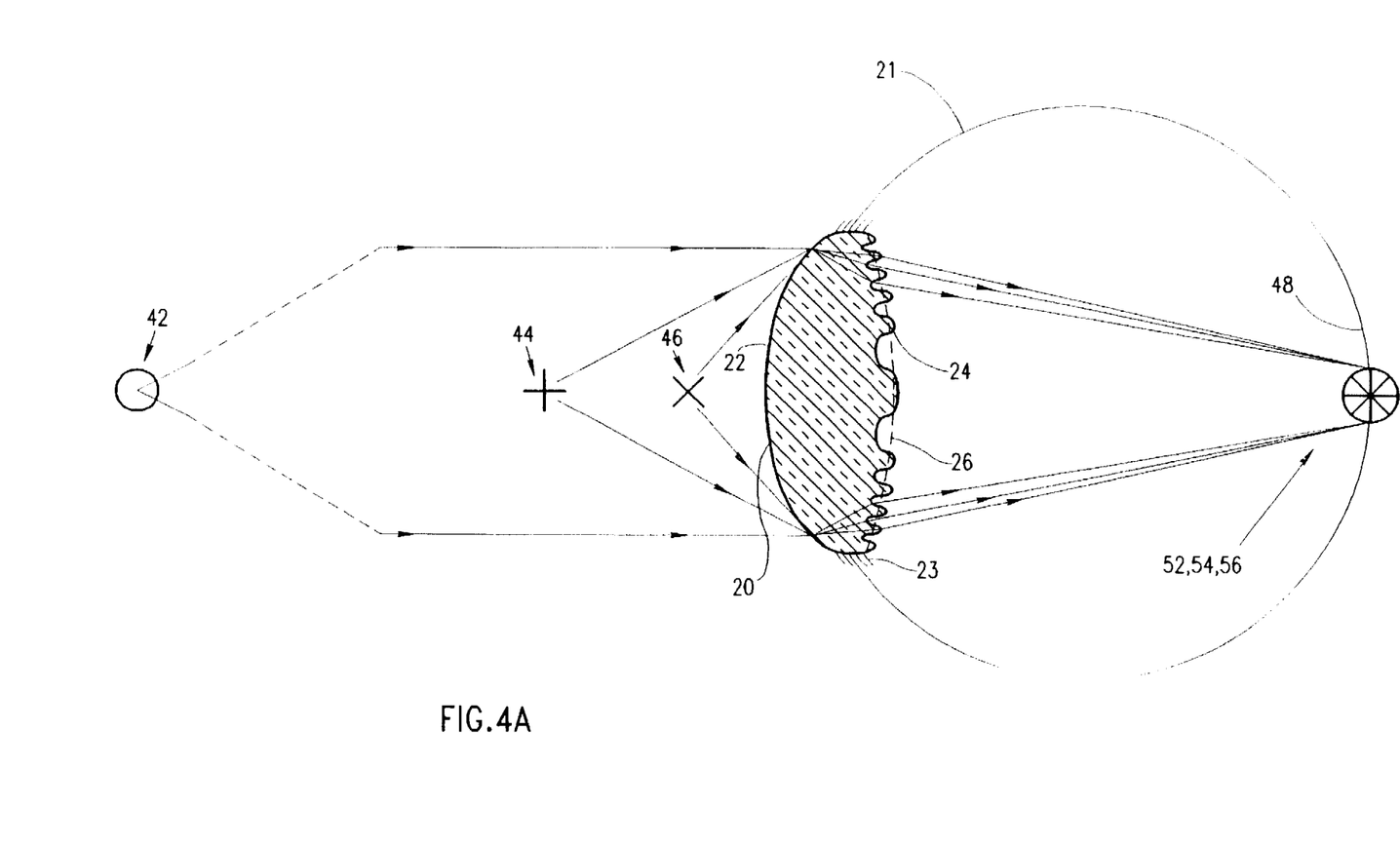
FIG. 4A is a schematic illustration of the optical effect of an intraocular lens in accordance with a preferred embodiment of the present invention.
Figure 4B:
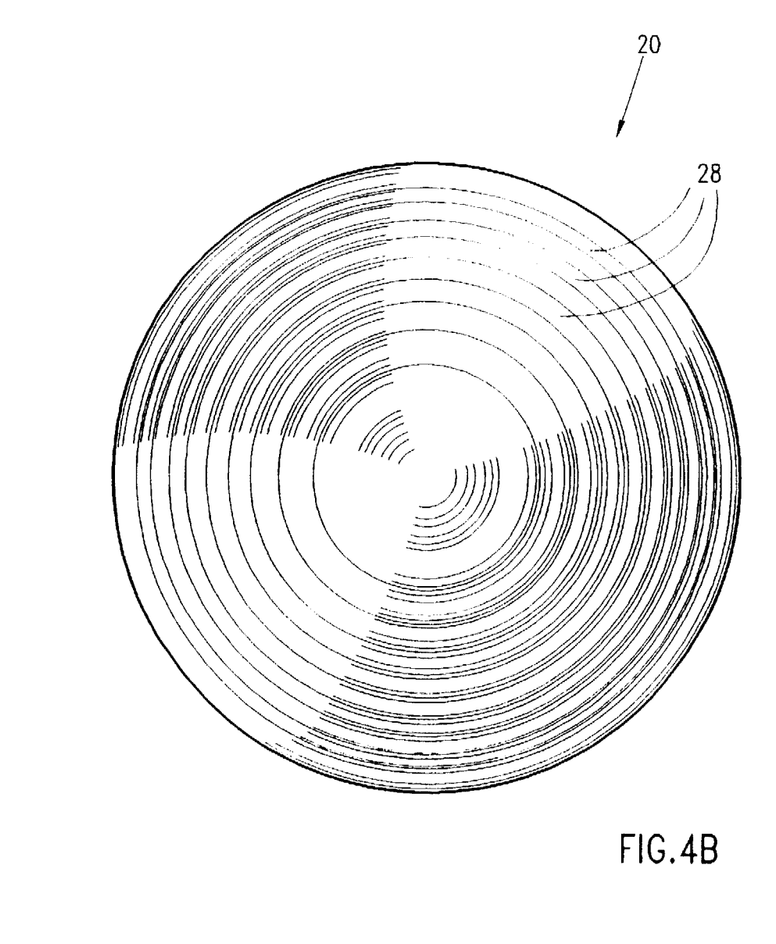
FIG. 4B is posterior view illustration of an intraocular lens constructed in accordance with preferred embodiments of the present invention.
Figure 4C:
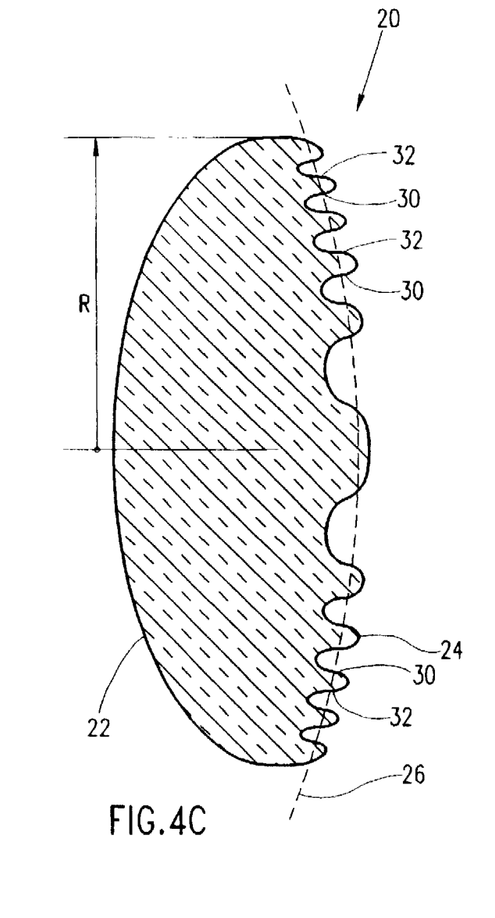
FIG. 4C is a radial, cross-sectional, illustration of the lens of FIG. 4A.

Reference is now made to FIG. 4A which shows an intraocular lens 20, in accordance with a preferred embodiment of the invention, which is installed in place of the lens of an eye. Lens 20 is attached to the interior of the eye 21 by attachment means 23 which may include sutures or other attachment materials as are known in the art. Lens 20 is preferably a tri-focal lens which is operative to focus images from infinity 42, from a middle distance 44 and from a reading distance 46 onto an imaging surface which is typically a retinal surface 48 of the eye. FIGS. 4B and 4C generally illustrate a posterior view and a radial cross section, respectively, of intraocular lens 20 constructed in accordance with a preferred embodiment of the present invention. As can be seen in FIG. 4C, lens 20 preferably includes a generally smooth, curved, anterior surface 22 and a preferably wavy posterior surface 24 having diffractive power. Surface 24 is preferably curved in accordance with a base reference surface 26 which, together with the surface 22, gives refractive focusing preferably equal to that required for focusing an image at middle distance 44 onto retinal surface 48.

The height of surface 24 fluctuates with respect to reference surface 26, which corresponds to the average curvature of surface 24. This varying height is operative, in accordance with a preferred embodiment of the invention, to form a multi-focal diffractive lens whose diffractive focusing power is superimposed on the refractive focusing power of the lens to form a tri-focal lens which focuses objects from far-distances 42, mid-distances 44 and near-distances 46 onto retinal surface 48.

In accordance with a preferred embodiment of the invention, the diffractive pattern is a locally periodic structure (which is periodic in $r^2$, not in r) which affects the phase of incident light, resulting in a corresponding, transverse, locally periodic, relative-phase structure of the exiting wave front. In contrast to prior art non-rectangular diffractive patterns, which typically consist of a series of one sided optical steps (as demonstrated in FIG. 2), each zone of the diffractive structure of the present invention is a substantially symmetric functions of $r^2$ with respect to a series of symmetry circles 28. Symmetry circles 28, whose spacing is also typically a function of $r^2$, are typically defined by a series of minima and maxima of the topographical height function along lens radius "r". The topographical height function is substantially constant along symmetry circles 28. The use of substantially two-sided, 30 and 32, periodic (in $r^2$) profile with optical height difference between minima and maxima substantially different from $\lambda/2$ creates two reciprocal dominant diffraction orders, namely a "+1" diffraction order and a "−1" diffraction order, in addition to a dominant undiffracted "0" order. These three dominant diffraction orders, which are generated by surface 24 of lens 20, are operative to focus incident light in accordance with three different foci. By a suitable choice of the topographical function of surface 24, the incident light energy can be distributed substantially evenly among the three diffraction orders. While the locally symmetric nature of a preferred topographical function results in a symmetric intensity distribution between orders "+1" and "−1", the relative intensities of those orders with respect to the "0" order may still be controlled by the amplitude of the function.

It should be appreciated that it is possible, in an alternative preferred embodiment of the invention to achieve an uneven distribution between orders "+1" and "−1" by using a topographical function in which the two sides 30 and 32 are not symmetric. Such a construction may be desired since, for example, reading and long distance viewing are performed at different light intensity levels and contrast.

Figure 5:
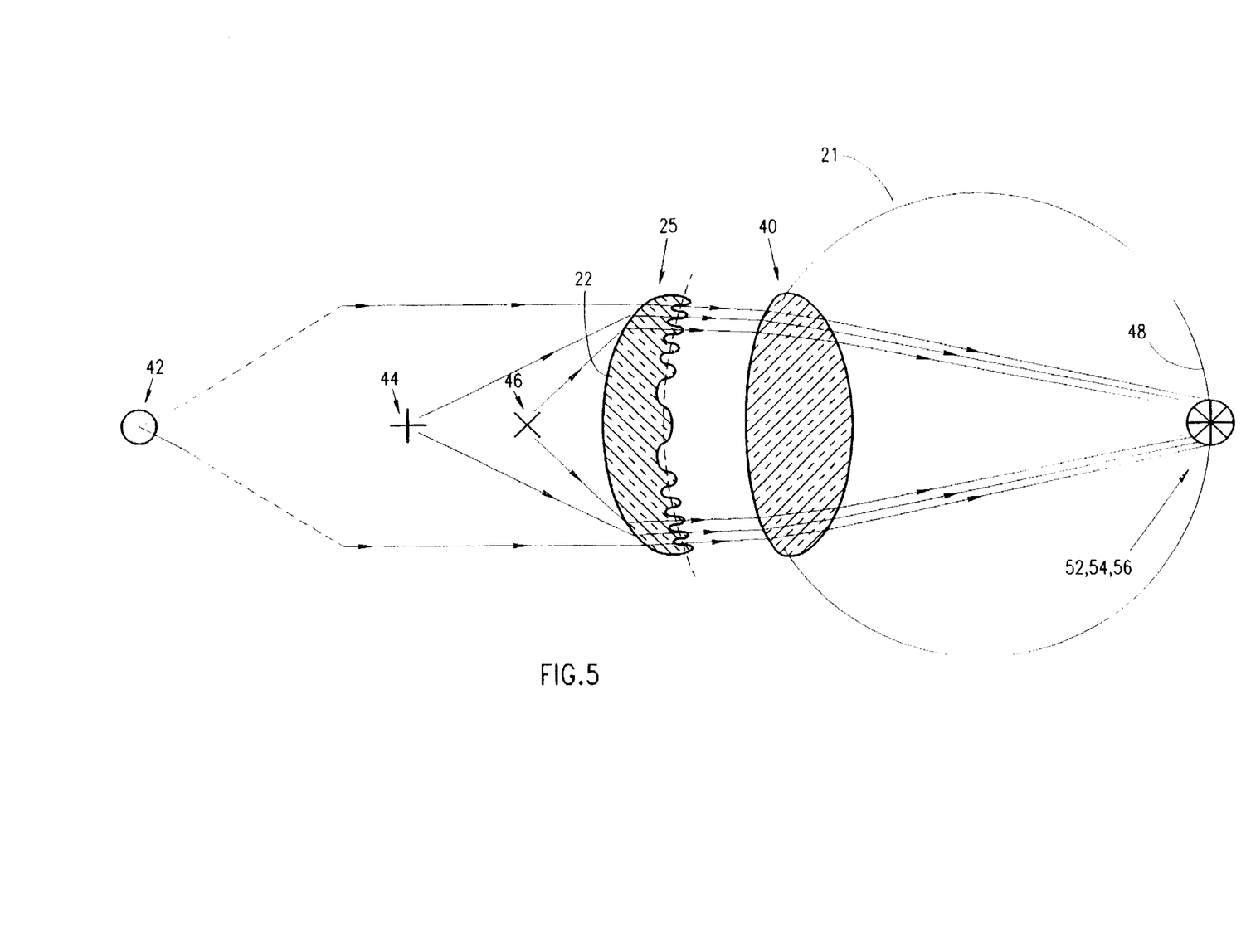
FIG. 5 is a schematic illustration of the optical effect of a contact lens in accordance with a preferred embodiment of the present invention when the lens is juxtaposed with a human eye lens.

Reference is now made to FIG. 5, which schematically illustrates the combined optical effect of a contact lens 25 in accordance with a preferred embodiment of the present invention and a human eye lens 40. In determining the desired refractive focal length of lens 25, lens 40 is assumed to be at a rest position and is assumed to be without adaptive capability, since the typical user of a trifocal lens has little focusing capability, so that multi-focal ability is primarily attributed to lens 25. Incident light "I" comes from objects 42, 44 and 46, which are located within a long distance range (typically infinity), an intermediate distance range and a short distance range (typically reading distance), respectively, from the user. The incident light is focused by the combined refractive optical power of lens 25, the diffractive optical power of surface 24, and the refractive power of eye lens 40 onto retina surface 48, forming thereon focused images 52, 54 and 56 which correspond to objects 42, 44 and 46, respectively.

In a preferred embodiment of the invention, most of the incident energy is contained in the three diffraction orders generated by diffractive surface 24, while other diffraction orders carry a negligible amount of light energy. It has been shown, experimentally and theoretically, that diffractive surfaces constructed in accordance with preferred embodiments of the present invention have such high light transmission efficiencies that the light intensity carried by any of the three dominant diffraction orders is sufficient for human vision. The "+1", "−1" and "0" orders conventionally represent the primary convergent order, the primary divergent order and the undiffracted light, respectively.

The refractive power of lens 20 (or lens 25), which is determined by the curvatures of surfaces 22 and 26, serves both as a base optical power for diffractive surface 24 and as a corrective optical element for lens 40 when the lens is a contact lens.

The refractive optical power of lens 20 (FIGS. 4A, 4C) is always convergent and generally speaking has the same convergence as the normal eye lens for focusing objects at middle distances onto the retina. In accordance with a preferred embodiment of the invention, light coming from objects at infinity is carried by the "−1" order, where the divergent nature of the "−1" diffractive order creates a virtual image of the infinite distance object at the middle distance wherein this virtual image is imaged on the retina by the refractive power of lens 20. Light from short (typically reading) distances is carried by the "+1" (convergent) order, that creates a virtual image of the short distance object at the middle distance, wherein this virtual image is imaged on the retina by the refractive power of lens 20 and light from the intermediate range is carried by the "0" (non-focusing) order and is imaged on the retina by the refractive power of lens 20.

For contact lenses, the refractive optical power of lens 25 is also generally convergent in order to compensate for the divergent "−1" order generated by surface 24. In accordance with a preferred embodiment of the invention, light coming from objects 46 at the short distance range (typically reading distance) is formed by the "+1" order into a virtual image at a middle distance, light from the intermediate range is passed unaltered by the "0" order and light from the long distance range is formed by the "−1" order into an image at the middle distance. Consequently, lens 40 focuses all three middle distance images onto the same image plane, i.e., the retina, forming a triple focused image thereon. If the user is incapable of focusing parallel rays (i.e. a near sighted user) or is farsighted, surface 22 may be constructed so as to provide lens 25 with further, corrective, refractive power, in accordance with the diopter number correction needed by the specific user such that the combined refractive power of lenses 25 and 40 focuses a middle distance image at the retina. Additionally, while the contact lens is illustrated as having the diffractive surface facing the cornea, where the diffractive surface is generally constructed to adapt to the curvature of a user's cornea, the diffractive surface may be part of the anterior surface of the contact lens.

Reference is now made to FIGS. 6–8C, which illustrate radial cross-sections of contact lenses or intraocular lenses constructed in accordance with preferred embodiments of the present invention. The preferred embodiments described hereinbelow are presented for illustrative purposes only and are not to be understood as limiting the scope of the present invention in any sense. For FIGS. 7A–8A only the diffractive surface is shown for simplicity. For FIGS. 8B and 8C, only a short, more enlarged, portion of the diffractive surface cross-section is shown.

Figure 6:
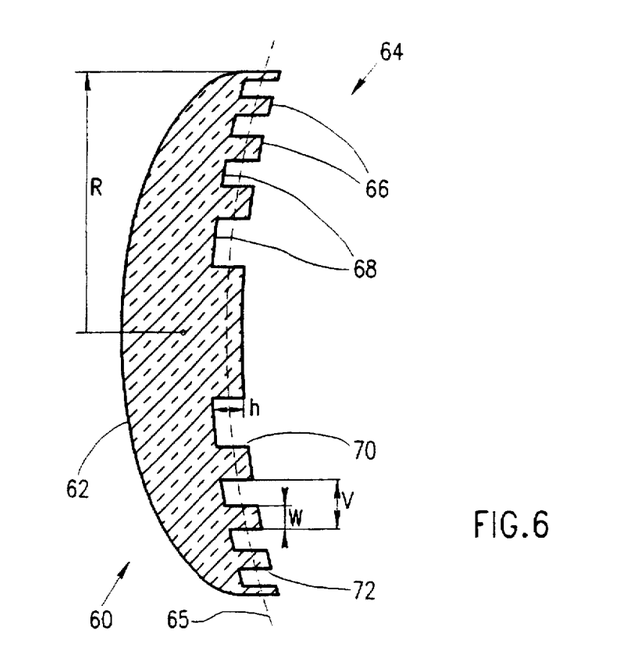
FIG. 6 is a radial, cross-sectional, illustration of a lens having a square wave diffractive surface topography, plotted as a function of r, the radial dimension, in accordance with a preferred embodiment of the invention.

Reference is made to FIG. 6, which illustrates a radial cross section of a lens 60, whose diffractive surface 64 substantially follows a square-wave topographical height function with respect to a generally smooth, curved, base reference surface 65, in accordance with a preferred embodiment of the present invention. The square wave function defines rectangular protrusions 66 and rectangular recesses 68 which are separated by step downs 70 and step ups 72. In contact lenses, reference surface 65 is generally constructed to adapt to the curvature of a user's cornea. The relative light intensities carried by the "+1", the "−1" and the "0" diffraction orders are generally controlled by the height "h" of steps 70 and 72 which determines the phase difference between light passing through protrusions 66 and light passing through recesses 68 close to any of steps 70 or 72, (i.e. the optical step) of the diffraction pattern. In some embodiments of the invention, it may also be desirable to vary the duty cycle of the topographic function, namely the ratio between width "W" of protrusions 66 and width "V" of the total cycle.

In accordance with the present embodiment, contrary to what has been generally believed in the past for bifocal square protrusion lenses, optimal light transmission efficiency for three foci is achieved when the optical height "$h_o$" is substantially less than $\lambda/2$, where $\lambda$ is the average or typical optical wavelength viewed with the lens.

According to a preferred embodiment of the invention when the optical height of the step is approximately $0.32\lambda$ and the duty cycle is 0.5, then the three refractive orders carry approximately even amount of light energy, with a total efficiency of about 86%. It is interesting to note that for a step type bi-focal lens the total efficiency is about 81%. The width of a cycle is preferably approximately $\lambda f/2r$.

According to an alternate embodiment of the present invention, when the optical step determined by steps 70 and 72 is equal to $\lambda/2$, a duty cycle of 0.26 should be used in order to achieve a substantially even distribution of light intensity between the three diffraction orders. The over all transmission efficiency obtained by such a lens is only approximately 66%.

Figure 7A:
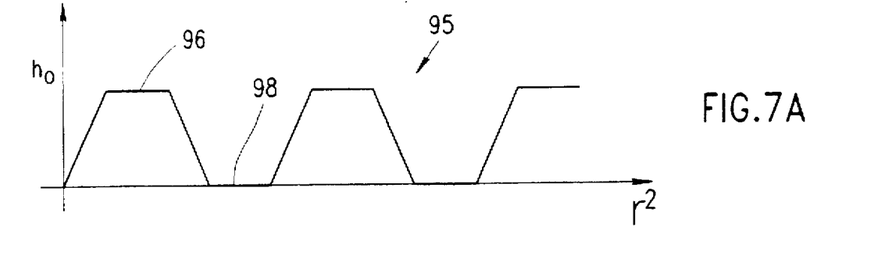
FIG. 7A is a radial, cross-sectional, illustration of the diffractive surface of a lens having a trapezoidal diffractive surface topography when plotted as a function of $r^2$, in accordance with a preferred embodiment of the invention.

Reference is now made to FIG. 7A, which illustrates a diffractive surface 95 on a radial cross section of a lens. Surface 95 substantially follows a trapezoidal-wave topographical height function with respect to the base reference surface, in accordance with another preferred embodiment of the present invention. FIG. 7A shows the cross-section as a function of $r^2$. When the function is plotted as a function of r, which is true radial distance, the function shown in FIG. 7B results. It is seen that the rising and falling portions of the function have a parabolic variation with r. The trapezoidal wave function defines trapezoidal protrusions 96 and trapezoidal recesses 98. The parameters which control the light intensities in this embodiment are: the phase delay (optical step) between protrusions 96 and recesses 98, and the radial distance "s" over which the surface topography gradually changes from recess to protrusion or vice versa. Again, the present invention has shown that optimal results are achieved with an optical step which is smaller than $\lambda/2$. Using an optical height of $0.369\lambda$, a slope up (and down) 0.2 of the period and upper and lower plateau of 0.3 of the period, an efficiency of approximately 92% was calculated, generating 30.7% of the total incident energy through each diffraction order. This surface topography is not only smoother than the surface of the square structure of FIG. 6 (all corners are more than 90 degree angles) but it is also more efficient. The width of a cycle is preferably approximately $\lambda f/2r$.

Figure 7B:
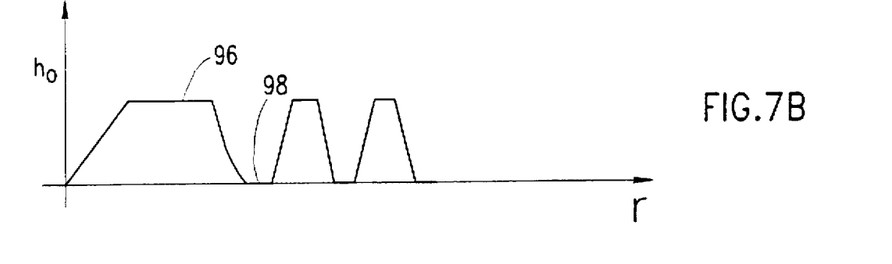
FIG. 7B is a radial, cross-sectional, illustration of the true topography of the lens of FIG. 7A plotted as a function of r, the actual radial dimension, in accordance with a preferred embodiment of the invention.
Figure 7C:
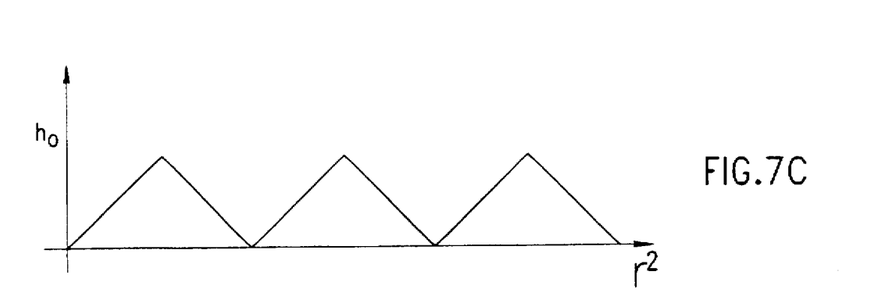
FIG. 7C is a radial, cross-sectional, illustration of the diffractive surface of a lens having a triangular diffractive surface topography when plotted as a function of $r^2$, in accordance with a preferred embodiment of the invention.

FIGS. 7C shows a surface topographical function where surface optical height has a triangular variation with $r^2$. The same function, plotted is true (r) space, has the shape shown in FIG. 7D, where the rising and falling portions both have parabolic shapes. The optimal optical height $h_o$ for such profiles are calculated as $0.579\lambda$. For this embodiment the total efficiency is approximately 85%, with each of the three orders having an efficiency of approximately 28%.

Figure 8A:
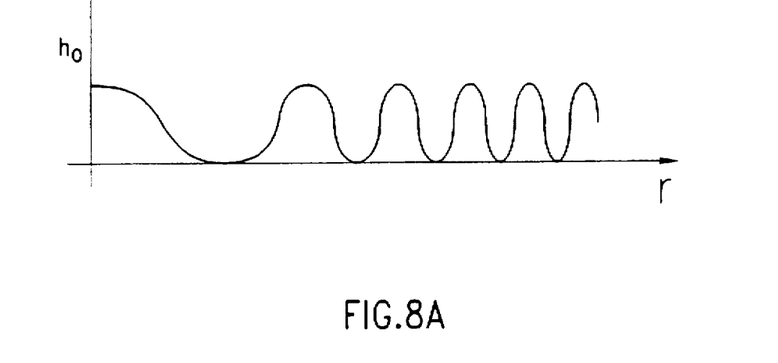
FIG. 8A is a radial, cross-sectional, illustration of the diffractive surface of a lens having a diffractive surface topography which follows a particular formula in accordance with one particularly preferred embodiment of the invention.

Reference is now made to FIG. 8A, which illustrate a radial cross section of a lens constructed in accordance with one particularly preferred embodiment of the invention. Unlike any of the previous embodiments described hereinabove, the surface topography function of a diffractive surface 104 is a smooth surface and has no discontinuities in the first (or higher) derivatives of the function. According to this preferred embodiment, the topographical optical height "$h_o(r)$" with respect to a reference surface at a radial distance "r" from center "C" of the lens is given by the formula:

$$h_o(r) = A \cdot \cos(k \cdot r^2 + \phi), \quad (1)$$

wherein:

$$k = \pi/(\lambda f); \quad (2)$$

and $$A = 0.228\lambda, \quad (3)$$

and wherein:

"$\lambda$" is the wavelength of light at the center of the typical bandwidth which is viewed with the lens (typically in the visible spectrum), "f" is the desired first order focal length, and $\phi$ is an arbitrary constant.

By using conventional mathematical methods, it has been shown that for a function such as equation (1), the amplitude "A" defined by equation (3) provides optimal light transmission efficiency together with a substantially even energy distribution among the three diffraction orders. The over all transmission efficiency achieved by this diffraction topography is over 90%. While this is slightly lower than the efficiency calculated for the trapezoidal topography, considering the extremely smooth surface which is provided by the topography of FIG. 8A, this topography is very preferable.

It should be appreciated that the topographical optical height function of the diffractive surface of a lens constructed in accordance with the present invention is not limited to the functions described hereinabove. In fact, other topographical functions, which can be determined by numerical methods, may prove to yield even more efficient results. For example, any different function "F(r)" of "r" may be substituted in equation (1) to replace "$k \cdot r^2$". The value of "A" can then be calculated in the following manner [the same procedure was used to determine the value of equation (3)]:

First, it is known that a function of the form $z(r) = A \cdot \cos[F(r)]$ spatially modulates the incoming wave front, so that the outgoing wave front follows the equation:

$$U(r) = U_o \cdot \exp\{i \cdot 2\pi/\lambda [n_2 - n_1] A \cos[F(r)]\}, \quad (4)$$

wherein "$\lambda$" is the center of the typical bandwidth which is viewed with the lens (typically in the visible spectrum), "$n_1$" is the refractive index of the lens and "$n_2$" is the refractive index of the surrounding medium. Equation (4) can be decomposed into:

$$U(r) = U_O \cdot \sum_{m=-\infty}^{\infty} i^m J_m[2\pi/\lambda(n_2 - n_1)A] \exp[imF(r)] \quad (5)$$

wherein "$J_m$" indicates the Bessel function coefficient of order m. Each component of the sum in (5) represents the effect of a single diffraction order, wherein "$J_m[2\pi/\lambda(n_2-n_1)A]$" controls the relative amplitude of the component and "$imF(r)$" ("i" indicates the imaginary part of the exponential function) determines its phase. In order to achieve an even distribution between the three orders, it is sufficient that the "0" order amplitude is equal to the "+1" order amplitude, since orders "+1" and "−1" have the same amplitude (due to the symmetry of the Bessel coefficients). Thus "A" should be chosen so that the following holds:

$$J_0[2\pi/\lambda(n_2-n_1)A] = J_1[2\pi/\lambda(n_2-n_1)A] \quad (6)$$

Equation (6) can be solved by numerical methods in order to obtain the optimal value of "A".

It should be noted that by selecting a different value of amplitude "A", the "0" order can be almost completely suppressed so that all the incident energy is divided between orders "+1" and "−1", thereby an efficient bi-focal lens can be achieved. Also, any other value of "A" may be selected in order to achieve other desired energy distributions between order "0" and orders "±1". Furthermore, by biasing the local symmetry of the topographical function, the relative intensities of orders "+1" and "−1" can be also continuously varied.

In adapting the diffractive lenses thus far described to uneven, high efficiency distributions of the incident light between the three orders, it has been found that changing the symmetry of the surface topographical function results in the following typical preferred embodiments of the invention.

For example in one preferred embodiment of the invention, the rising and falling slopes "S" of the trapezoidal function illustrated in FIGS. 7A and 7B are varied to achieve uneven, but highly efficient tri-modal diffraction. In one particular embodiment the rising slope is 0.132 of the period and the falling slope is 0.264 of the period (referenced to $r^2$). The upper and lower plateau are each 0.302 of the period. The height of the trapezoid is 0.398λ. For this embodiment the calculated energy distribution between the three orders is order "0"=0.240, order "+1"=0.271 and order "−1"=0.390 for a total efficiency of about 90%. This distribution is believed to be better suited for matching with the light levels generally available for different tasks than is the even distribution. Other distributions are of course possible with other choices of "S" and optical height.

With the sinusoidal profile, the period is constructed of two parts each of the general form of equation (1) except that, for a preferred embodiment of the invention, in the falling half cycle, the spatial frequency is increased so that the radial distance taken up by this portion is only 45% of the period. In the rising half cycle, the spatial frequency is decreased so that the function requires 55% of the cycle. For this embodiment the calculated energy distribution between the three orders is order "0"=0.234, order "+1"=0.288 and order "−1"=0.350 " for a total efficiency of 87.2%.

Figure 9:
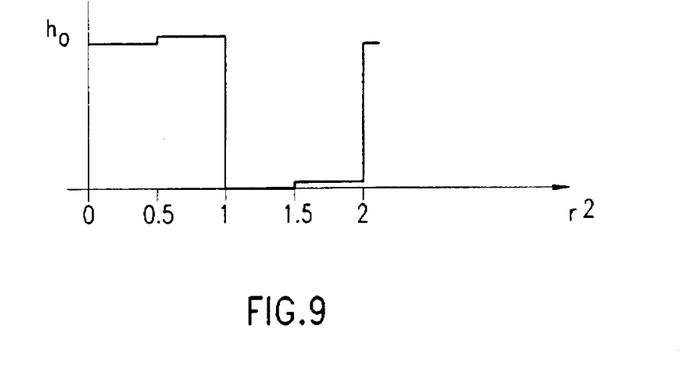
FIG. 9 is a detail of one cycle of the diffractive surface of a square wave type diffraction lens of the present invention, adapted for uneven division of light between three dominant diffraction orders.

For the rectangular embodiment, the asymmetry is preferably achieved by adding an additional step over a portion, preferably half, of both the upper and lower portions of the topographical function (as shown in FIG. 9 as a function of $r^2$). For a particular preferred embodiment of the invention, the large step $h_1$ has an optical height 0.345λ with each of the smaller steps having an optical height of 0.05λ. For this embodiment the calculated energy distribution between the three orders is order "0"=0.217, order "+1"=0.267 and order "−1"=0.366 for a total efficiency of 85%.

Figure 7D:
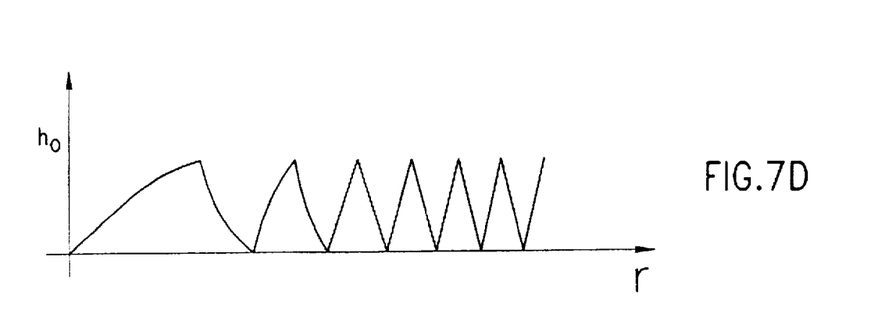
FIG. 7D is a radial, cross-sectional, illustration of the true topography of the lens of FIG. 7C plotted as a function of r, the actual radial dimension, in accordance with a preferred embodiment of the invention.

For a preferred triangular profile the rising portion extends over 0.425 of the period and the falling portion extends over 0.575 of the period. The optical height is preferably 0.625λ. For this embodiment the energy distribution between the three orders is order "0"=0.215, order "+1"=0.238 and order "−1"=0.353 for a total efficiency of 80.6%.

It must be remembered that all of the radial distances are scaled to $r^2$ and not to r.

Figure 8B:
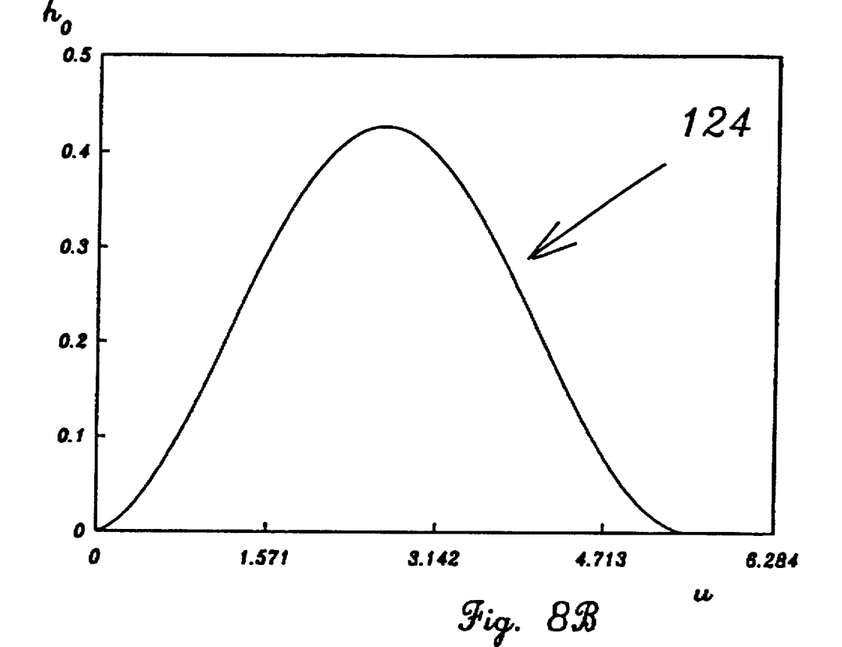
FIG. 8B is a radial, cross-sectional, illustration of part of the diffractive surface of a lens having a diffractive surface topography which follows a particular formula in accordance with another preferred embodiment of the invention.
Figure 8C:
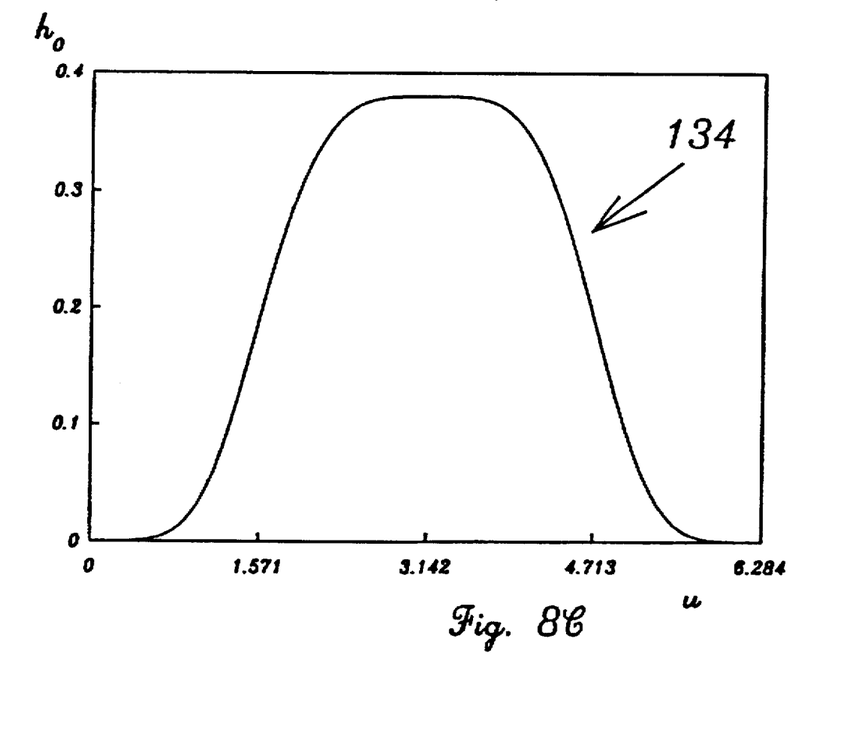
FIG. 8C is a radial, cross-sectional, illustration of part of the diffractive surface of a lens having a diffractive surface topography which follows a particular formula in accordance with yet another preferred embodiment of the invention.

Reference is now made to FIGS. 8B and 8C, which relate to additional, particularly preferred, embodiments of the present invention. FIG. 8B illustrates a cross section of a portion of the diffractive surface 124 of a polynomialtopography lens constructed in accordance with a particularly preferred embodiment of the invention. FIG. 8C illustrates a cross-section of a portion of the diffractive surface 134 of a super-Gaussian-topography lens constructed in accordance with another particularly preferred embodiment of the invention. As in the embodiment of FIG. 8A, the surface topography functions describing the preferred surfaces of FIGS. 8B and 8C are both smooth and have no discontinuities in the first (or higher) derivatives of the functions.

In the embodiment of FIG. 8B, the topographical optical height "$h_o(r)$" with respect to a reference surface at a radial distance "r" from center "C" of the lens is a periodic function of $r^2$. Within each period of $h_o(r)$, the topographical height, $h_o(u)$, with respect to a normalized periodic variable, $u(r^2+\delta)$ wherein δ is a constant, is given by:

$$h_o(u) = \sum_{i=1}^{n} a_i u^i,\quad (7)$$

wherein the $a_i$ coefficients are calculated using numerical optimization method. The variable "u", which will be hereinafter referred to as the normalized periodic variable, is equal to zero at the beginning of each period of $h_o(r)$, and equal to 2 π at the end of each period. As in the In accordance with a preferred embodiment of the invention, the $a_i$s which are selected are those that yield a transmission efficiency distribution, among the diffraction orders, as close as possible to preselected target values chosen for the different orders. Any optimization method known in the art may be used to calculate the proper $a_i$s. The surface topography illustrated in FIG. 8B will be hereinafter referred to as the polynomial surface topography.

It is appreciated that, contrary to the sinusoidal embodiment of FIG. 8A, the function defining the outgoing wave front of the polynomial surface cannot be determined analytically by a procedure of the type used in equations (4) to (6). Therefore, the functional behavior of the outgoing wavefront must be determined numerically, preferably by using ray-tracing techniques, as is well known in the art. In a preferred embodiment of the invention, the following procedure is used to calculate the proper $a_i$s:

First, an order "n" is chosen for the polynomial function. Then, n arbitrary initial values are given to the n respective $a_i$s. The transmission efficiencies of the dominant diffraction orders are then calculated, numerically, as discussed in the previous paragraph. Then, the calculated efficiency of each of the dominant diffraction orders is subtracted from the corresponding preselected target value, yielding a respective efficiency error for each of the dominant orders. An error optimizing function, such as the sum of the squares of the efficiency errors or any other desired function of the errors, is then constructed. Finally, the $a_i$s are adjusted by a standard search procedure, such as "steepest slope", so that the value of the error optimizing function is reduced.

The procedure described in the previous paragraph is preferably repeated until the value of the efficiency error optimizing function is below a preselected maximum value. The resultant surface topography function may be locally symmetric, typically when the target values represent an equal efficiency distribution among the participating orders, or locally asymmetric, when uneven target values are chosen.

For a polynomial of degree six (n=6), as an example, wherein $a_1$=3.17·10⁻², $a_2$=0.17, $a_3$=−0.03, $a_4$=−1.53·10⁻², $a_5$=4.29·10⁻³ and $a_6$=−2.86·10⁻⁴, efficiencies of 30.5%, 30% and 30%, were calculated for the "0", "+1" and "−1" diffraction orders, respectively. It should be appreciated that this high transmission efficiency (a total efficiency of 90.5% ) may be further increased by careful search of proper $a_i$s and/or by selecting a different polynomial order "n".

By proper choice of the $a_i$s, it is also possible to produce uneven efficiency distributions. For example, when n=6, $a_1$=−8.43·10⁻³, $a_2$=−8.46·10⁻², $a_3$=0.13, $a_4$=−3.85·10⁻², $a_5$=4.13·10⁻³ and $a_6$=−1.32·10⁻⁴, the resultant efficiencies are 22%, 30% and 35%, for the "0", "+1" and "−1" diffraction orders, respectively. The total efficiency of this embodiment is 87%. It should be appreciated that other choices of $a_i$s may yield a higher efficiency.

In the embodiment of FIG. 8C, the topographical optical height "$h_o(r)$" with respect to a reference surface at a radial distance "r" from center "C" of the lens is a periodic function of $r^2$. Within each period of $h_o(r)$, the topographical height, "$h_o(u)$", with respect to the periodic variable $u(r^2+\delta)$ is given by the formula:

$$H \cdot \exp\{-[(u-\pi)/W]^n\},\quad (8)$$

wherein the parameters H, W and n are optimized using numerical optimization methods and wherein u is the normalized periodic variable, as explained above with reference to the embodiment of FIG. 8B. The surface topography illustrated in FIG. 8C will be hereinafter referred to as the super-Gaussian surface topography. In this embodiment, as in the polynomial embodiment, an arbitrary order "n" is chosen for the super-Gaussian. The parameters H and W are then optimized, using numerical methods, to yield a preselected target efficiency distribution among the dominant orders. It should be appreciated that the numerical optimization procedure in this embodiment is relatively simple, because the super-Gaussian topography is completely determined by only three parameters.

For example, an efficient equal distribution between three diffraction orders is achieved with a super-Gaussian topography in which H=0.38 W=0.55 $\pi$ and n=4. The transmission efficiencies of the "0", "+1" and "−1" diffraction orders, in this embodiment, are 30.9%, 30.8% and 39.8%, respectively, for a total of 92.5%.

Alternatively, for an asymmetric distribution of transmission efficiencies, an asymmetric super Gaussian may be used. The asymmetric Super-Gaussian follows the formula:

$$H \cdot \exp\{[(u-u_0)/W_1]^{n_1}\} \text{ for } u \leq u_0; \quad (9)$$

and $$H \cdot \exp\{[(u-u_0)/W_2]^{n_2}\} \text{ for } u \geq u_0 \quad (9)$$

wherein $u_0=2\pi W_1/(W_1+W_2)$ ($0 \leq u_0 \leq 2\pi$) and wherein, H, $W_1$, $W_2$, $n_1$, and $n_2$ are all preselected constants. "u" is the normalized periodic variable defined above in equations (7) and (8). The parameters H, $W_1$, $W_2$, $n_1$ and $n_2$ are optimized using the numerical optimization methods described hereinabove.

For example, an efficient unequal distribution between three diffraction orders is achieved with an asymmetric Super-Gaussian topography in which H=0.406, $W_1$=0.44 $\pi$, $W_2$=0.64 $\pi$ and $n_1$=$n_2$=4. The transmission efficiencies of the "0", "+1" and "−1" diffraction orders, in this embodiment, are 26%, 29% and 36%, respectively, for a total transmission efficiency of 92%.

It should be appreciated that, due to the relatively few parameters used by the super-Gaussian and the relatively well-behaved response of the Gaussian to changes in the parameters, the relative efficiencies of the dominant diffraction orders can be accurately controlled.

It is a feature of certain embodiments of the present invention that the diffractive surface of a contact lens may be at the posterior side, i.e. the side which faces the human eye cornea. This is possible due to the relatively smooth surfaces provided by preferred embodiments of the present invention, such as described hereinabove. However, it should be appreciated that in a variety of embodiments of the invention, each or both of the anterior and posterior surfaces may be appropriately constructed to have diffractive properties.

It should be appreciated that in many preferred embodiments of the present invention, particularly in the embodiments described with reference to FIGS. 8A–8C, the diffractive surface topography is much smoother than any of the prior art surfaces. More particularly, in preferred embodiments of the present invention, the radius of curvature of the diffractive surface at any point on the surface is equal to at least twice the step height (i.e. the difference in topographical height between the nearest local maximum and the nearest local minimum) and, more preferably, 10 to 100 times the step height.

Figure 10A:
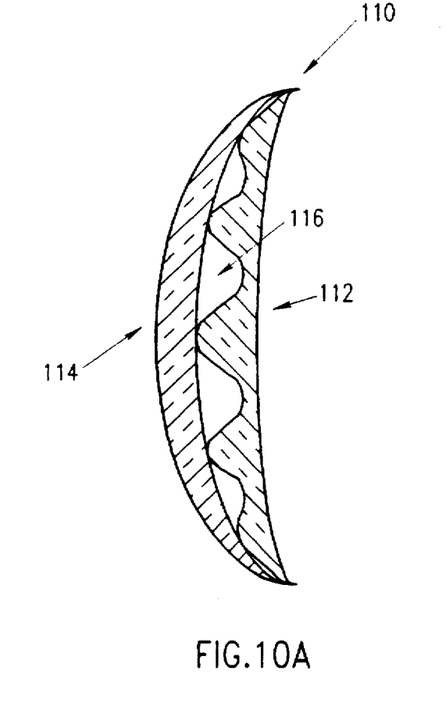
FIG. 10A and 10B show two sandwich type contact lens forms of the present invention.
Figure 10B:
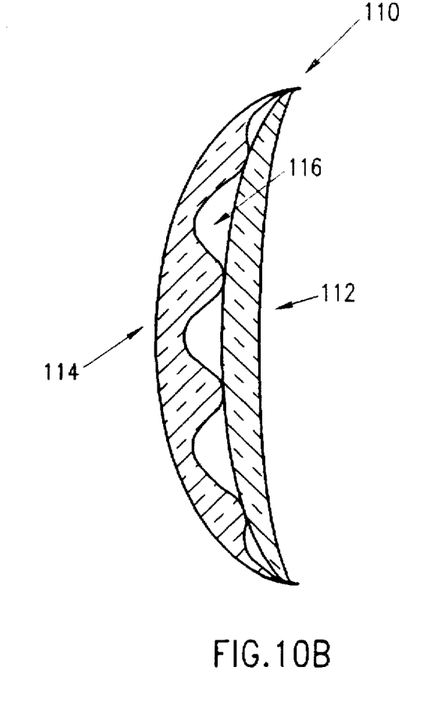

In further preferred embodiments of the invention, illustrated in FIGS. 10A and 10B, a contact lens 110 is a composite lens made up of a first portion 112, similar in structure to lens 25 and a second portion 114 having smooth anterior and posterior surfaces. An interior space 116 is preferably sealed from the outside by sealing the edges of portions 112 and 114 and generally contains air or a liquid having a refractive index substantially different from that of portions 112 and 114. The refractive power of the lenses may be the result of either portions 112 or 114 or both. Preferably, the top of the diffractive surface touches the facing smooth surface of the facing portion, thereby spacing the two portions and forming a well defined optical structure.

In a preferred embodiment of the invention, two different materials are used for portions 112 and 114. More preferably, inner portion 112, facing the cornea, is formed of a relatively soft material which is convenient to the eye and portion 114 is formed of relatively hard material. In this preferred embodiment, the diffractive surface is preferably formed on the inner surface of portion 114, which is generally the more stable portion. The outside surface of portion 112 is adapted for contact with the cornea of an eye of a user.

In accordance with a preferred embodiment of the present invention, any of the multi-focal lenses described above may include at least one aspheric surface. The aspheric surface is operative to compensate for optical aberrations, which are typical of spherical surfaces, especially near the edge of the lens. In a preferred embodiment, the aspheric surface is the posterior surface of the lens and, more preferably, the posterior surface is shaped in accordance with the aspheric surface of the human cornea. The aspheric optical properties of the aspheric surface may be provided by refractive power, diffractive power or both. Aspheric properties can be added to the diffractive surface of the lens by shifting the radial locations of the optical steps on the surface, with respect to the normal (spherical) diffraction pattern, by precalculated amounts.

In one preferred embodiment of the invention, the curvature "z(r)" of the lens at a distance "r" from the center of the lens is given by the formula:

$$z(r)=cr^2/\{1+[1-(k+1)c^2r^2]^{1/2}\}+\Sigma b_n r^n, \quad (10)$$

wherein "c" is the curvature of the lens at its center and "k" and $b_n$ are aspheric parameters.

In some applications of the lenses of the present invention, as thus far described, the diameter of the lens is very small. Therefore, remembering that the diffractive surfaces are generally defined by locally periodic functions, the number of periods across the diameter may be very small (typically less than ten). In these cases, the performance of the lens may be affected by the phase of the locally periodic functions which define the surface topography. The phase $\phi$ defined in equation (1), for example, should not be arbitrary when the number of periods is small but, rather, it should be experimentally adjusted to yield optimal imaging efficiency. Such optimal efficiency depends on the application, but may provide for a greater proportion of the incident light going into one or two of the orders at the expense of the other(s). Similarly, variations may be made in the phase $\delta$ of the periodic coordinate $u(r^2+\delta)$ of equations (7), (8) and (9) to tailor the division of light at small apertures. It should be appreciated that even when the number of periods across the diameter is sufficiently large, the effective number of periods in use may be very small. This may be the case, for example, in contact lenses when the pupils are very small.

It should be appreciated that the present invention is not limited to the descriptions brought hereinabove. Rather the scope of the invention is defined only by the following claims:

We claim:

1. A multi-focal diffractive lens having a diffractive surface and a plurality of diffractive orders, the surface having an optical height, $h_o$, relative to a bese reference surface which is a periodic function, each period of which is given by:

$$H \cdot \exp\{[(u-u_0)/W_1]^{m_1}\} \text{ for } u \leq u_0;$$

and $$H \cdot \exp\{[(u-u_0)/W_2]^{m_2}\} \text{ for } u \geq u_0,$$

wherein $u_0 = 2\pi W_1/(W_1+W_2)$, wherein H, $W_1$, $W_2$, $m_1$ and $m_2$ are preselected constants, wherein $W_1$ may be the same as or different from $W_2$ and $m_1$ may be the same as or different from $m_2$, wherein u is a function of r namely u(r) and, wherein the imaging efficiency of each of the diffractive order is not less than twenty percent.

2. A multi-focal lens according to claim 1 wherein the fraction of the total incident energy carried by each of three of the dominant orders is substantially equal.

3. A multi-focal lens according to claim 1 wherein the phase of said periodic function is preselected so as to provide a different proportion of the incident light to at least one of the foci at different lens openings.

4. A multi-focal diffractive lens according to claim 1 comprising a diffractive surface, having a surface topography including local minima and maxima, operative to focus light in accordance with a plurality of dominant diffraction orders defining a plurality of respective foci, wherein the imaging efficiency of each of the orders is not less than twenty percent and wherein the radius of curvature of the diffractive surface, at any given point on the surface, is equal to at least twice the difference in topographical height between the local minimum nearest to the given point and the local maximum nearest to the given point.

5. A multi-focal lens according to claim 4 wherein the radius of curvature of the diffractive surface, at any given point on the surface, is equal to at least ten times the difference in topographical height between the local minimum nearest to the given point and the local maximum nearest to the given point.

6. A multi-focal lens according to claim 1 wherein the lens is a contact lens adapted for placement on the cornea of a wearer.

7. A multi-focal lens according to claim 1 wherein the lens is an intraocular lens adapted for replacement of the natural lens of a wearer.

8. A multi-focal lens according to claim 1 comprising a first portion and a second portion each having two surfaces and an edge, wherein the diffractive surface comprises a surface of the first portion facing a surface of the second portion.

9. A multi-focal lens according to claim 8 wherein the diffractive surface touches the facing surface of the second portion, and wherein the edges of the two portions are sealed to form a sandwich structure having the diffractive surface interior to the sandwich.

10. A multi-focal lens according to claim 1 usable with light within a given wavelength band, wherein the band is represented by a typical wavelength.

11. A multi-focal lens according to claim 10 wherein the typical wavelength is approximately equal to 0.555 micrometers.

12. A multi-focal lens according to claim 6 comprising a refractive surface.

13. A multi-focal lens according to claim 7 comprising a refractive surface.

14. A multi-focal lens according to claim 1 wherein the lens is a contact lens adapted for placement on the cornea of a wearer.

15. A multi-focal lens according to claim 3 wherein the lens is a contact lens adapted for placement on the cornea of a wearer.

16. A multi-focal lens according to claim 1 comprising a first portion and a second portion each having two surfaces and an edge, wherein the diffractive surface comprises a surface of the first portion facing a surface of the second portion.

17. A multi-focal lens according to claim 3 comprising a first portion and a second portion each having two surfaces and an edge, wherein the diffractive surface comprises a surface of the first portion facing a surface of the second portion.

18. A multi-focal lens according to claim 1 wherein the sum of the efficiencies of three of the diffractive orders is at least 85%.

19. A multi-focal lens according to claim 3 wherein the sum of the efficiencies of three of the diffractive orders is at least 85%.

20. A multi-focal lens according to claim 1 and further comprising a refractive surface.

21. A multi-focal lens according to claim 3 and further comprising a refractive surface.

22. A multi-focal diffractive lens according to claim 4 wherein the radius of curvature of the diffractive surface, at any given point on the surface, is equal to at least fifty times the difference in topographical height between the local minimum nearest to the given point and the local maximum nearest to the given point.

23. A multi-focal diffractive lens comprising a diffractive surface, having a surface topography including local minima and maxima, operative to focus light in accordance with a plurality of dominant diffraction orders defining a plurality of respective foci, wherein the surface topography of the diffractive surface has no discontinuities in the first derivative;

wherein the imaging efficiency of each of the dominant orders is not less than twenty percent, and wherein the radius of curvature of the diffractive surface, at any given point on the surface, is equal to at least twice the difference in topographical height between the local minimum nearest to the given point and the local maximum nearest to the given point.

24. A multi-focal lens according to claim 23 wherein the radius of curvature of the diffractive surface, at any given point on the surface, is equal to at least ten times the difference in topographical height between the local minimum nearest to the given point and the local maximum nearest to the given point.

25. A multi-focal lens according to claim 23 wherein the radius of curvature of the diffractive surface, at any given point on the surface, is equal to at least fifty times the difference in topographical height between the local minimum nearest to the given point and the local maximum nearest to the given point.

26. A multi-focal lens according to claim 23 wherein the fraction of the total incident energy carried by each of the dominant orders is substantially equal.

27. A multi-focal lens according to claim 23 wherein the lens is a contact lens adapted for placement on the cornea of a wearer.

28. A multi-focal lens according to claim 23 comprising a first portion and a second portion each having two surfaces and an edge, wherein the diffractive surface comprises a surface of the first portion facing a surface of the second portion.

29. A multi-focal lens according to claim 24 comprising a first portion and a second portion each having two surfaces and an edge, wherein the diffractive surface comprises a surface of the first portion facing a surface of the second portion.

30. A multi-focal lens according to claim 23 wherein the sum of the efficiencies of three of the dominant diffraction orders is at least 85%.

31. A multi-focal lens according to claim 24 wherein the sum of the efficiencies of three of the dominant diffraction orders is at least 85%.

32. A multi-focal lens according to claim 25 wherein the sum of the efficiencies of three of the dominant diffraction orders is at least 85%.

33. A multi-focal lens according to claim 23 and further comprising a refractive surface.

34. A contact lens comprising:
 a first portion and a second portion each having two surfaces and an edge, wherein at least one surface of one of the portions comprises a diffractive surface wherein the diffractive surface faces a surface of the second portion, wherein the two portions are sealed to form a sandwich structure having a sealed third interior portion which is filled with a liquid and having the diffractive surfaces interior to the sandwich and wherein one of outer surfaces of the sandwich structure is adapted to contact the cornea of a user.

35. A contact lens according to claim 34 wherein the diffractive surface touches the facing surface of the second portion.

36. A composite contact lens comprising:
 a first portion and a second portion forming a sandwich structure;
 said first portion having at least one optical element in relief thereon;
 said second portion having generally smooth interior and exterior surfaces; wherein said interior surface faces said optical element; wherein the top of the relief of the optical element touches the interior surface thereby spacing the two portions and forming a well defined optical structure and wherein the optical structure between the two portions is filled with a liquid.

37. A lens according to claim 36 and wherein the spacing between said two portions defines a sealed interior portion.

38. A contact lens according to claim 36 wherein the optical element in relief is a diffractive element.

39. A composite contact lens comprising:
 a first portion and a second portion forming a sandwich structure;
 said first portion having at least one optical element in relief thereon;
 said second portion having at least one smooth surface facing said optical element; wherein the distance from a point on said facing surface, opposite the base of the relief of said optical element, is substantially equal to the height of the top of the relief;
 wherein the sandwich structure between the first portion and second portion is filled with a liquid.

40. A contact lens according to claim 39 wherein the optical element in relief is a diffractive element.

* * * * *